United States Patent [19]

Hansen et al.

[11] Patent Number: 5,079,243
[45] Date of Patent: Jan. 7, 1992

[54] BENZAZEPINES

[75] Inventors: Louis B. Hansen, Vaerlose; Kristian T. Hansen, Copenhagen, both of Denmark

[73] Assignee: Novo Nordisk A/S, Bagsvaerd, Denmark

[21] Appl. No.: 477,284

[22] Filed: Feb. 8, 1990

[30] Foreign Application Priority Data

Feb. 14, 1989 [DK] Denmark ............................ 0674/89

[51] Int. Cl.$^5$ .................. C07D 405/04; C07D 223/16; A61K 31/55
[52] U.S. Cl. ..................................... 514/213; 540/594; 540/595
[58] Field of Search ................. 540/594, 595; 514/213

[56] References Cited

U.S. PATENT DOCUMENTS

| | | | |
|---|---|---|---|
| 3,393,192 | 7/1988 | Walter et al. | 540/595 |
| 4,187,314 | 2/1980 | Holden et al. | 540/594 |
| 4,349,472 | 9/1982 | Gold et al. | 540/595 |
| 4,751,222 | 6/1988 | Bragstrup et al. | 514/213 |

FOREIGN PATENT DOCUMENTS

| | | | |
|---|---|---|---|
| 5298 | 11/1979 | European Pat. Off. | 514/213 |
| 5300 | 11/1979 | European Pat. Off. | 514/213 |
| 1268243 | 3/1972 | United Kingdom . | |

OTHER PUBLICATIONS

Hansen et al. Chemical Abstracts, vol. 112, 1990 Abstract 118677K.
Berger et al. Chemical Abstracts, vol. 110, 1989 Abstract 75345q.

*Primary Examiner*—Mukund J. Shah
*Assistant Examiner*—E. C. Ward
*Attorney, Agent, or Firm*—Steve T. Zelson; Elias J. Lambiris

[57] ABSTRACT

Novel 2, 3, 4, 5-tetrahydro-1H-3-benzazepines, which in the 7-position have a methoxymethyloxy group, in the 8-position hydrogen, halogen, or a nitro group and in the 5-position have an optionally substituted phenyl ortho-fused ring-system, with interesting effects on the central nervous system.

12 Claims, No Drawings

BENZAZEPINES

This invention relates to novel methoxymethyl ethers of 2,3,4,5-tetrahydro-1H-3-benzazepines and pharmaceutically acceptable acid addition salts thereof, to methods for their preparation, to pharmaceutical compositions containing them, and to their use in the treatment of certain disorders in the central nervous system.

In the last decade intensive pharmacological research concerning benzazepines has taken place. The pharmacological properties of benzazepines depend to a large extent on the substituents. Various substituted benzazepines exhibiting neuroleptic, anti-aggressive, anti-Parkinson and vascular effects are known.

In U.S. Pat. No. 3,393,192 (Schering Corp.) derivatives of 5-phenyl-2,3,4,5-tetrahydro-1H-3-benzazepine having, inter alia, hydroxy, lower alkoxy or halogen in the 7- and/or 8-position are described.

These compounds are claimed to be useful as antibacterials, antidepressants, antihypertensives and analgetics.

In U.S. Pat. No. 4,751,222 (NOVO Industri A/S) 2,3,4,5-tetrahydro-1H-3-benzazepines having a heterocyclic or an ortho-fused heterocyclic ringsystem in the 5-position are described. These compounds are claimed to have antipsychotic and antidepressive effects.

In GB patent specification 1,268,243 (Wallace & Tiernan Inc.) various 1,2,4-5-tetrahydro-3H,3-benzazepines are described as useful analgetics.

The present invention describes methoxymethyl ethers of 2,3,4,5-tetrahydro-1H-3-benzazepin-7-ols with various substituents in the 5-position having interesting effects on the dopaminergic central nervous system.

The 7-methoxymethyloxy-2,3,4,5-tetrahydro-1H-3-benzazepines of the invention has the general formula I

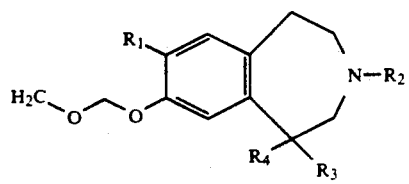

wherein
- $R^1$ is hydrogen, halogen or nitro
- $R^2$ is hydrogen or $C_{1-6}$-alkyl
- $R^3$ is hydrogen or $C_{1-6}$-alkyl
- $R^4$ is furyl, thienyl, pyridyl or ringsystems consisting of phenyl ortho condensed with a benzen, cyclohexan, cyclohexen, cyclopentan or cyclopenten ring in which rings one of the carbon atoms may be exchanged with oxygen, sulphur or nitrogen and pharmaceutically acceptable acid addition salts thereof, exhibits useful pharmacological properties by action on the central dopaminergic system.

Compounds of the general formula I exhibit strong antidopaminergic effect. Thus, they potently inhibit stereotyped gnawing behaviour in mice induced by methylphenidate (i.e Acta Pharmacol. Toxicol. 31, 1972, 488), and they also inhibit conditioned avoidance response and amphetamine cue in rats.

The compounds of formula I may be presented as a mixture of optical isomers which may be resolved into the individual pure isomers. This resolution may conveniently be performed by fractional crystallization, from various solvents of the salts of compounds of the formula I with optical active acids or by other methods known from the literature, e.g. chiral column chromatography. Therefore, this invention includes all isomers, whether resolved or mixtures thereof.

Particularly valuable embodiments of this invention are non-toxic, pharmaceutically acceptable acid addition salts of benzezepines of formula I. Such salts include those derived from inorganic and organic acids such as hydrochloric, hydrobromic, sulphuric, phosphoric, methanesulfonic, acetic, lactic, maleic, phthalic and tartaric acids.

These salts may be prepared by methods known to professionals skilled in the art.

The compounds of this invention are formulated into conventional pharmaceutical compositions according to known techniques. The dosage formulation will preferably contain the active compounds in the range of 0.5 mg to about 1000 mg for oral dosing. Typical dosage for antipsychotic effect would vary between about 0.5 to 10 mg/kg per day divided in 2 or 3 doses, administered orally.

The pharmaceutical carriers employed can be conventional solid or liquid carriers. Examples of solid carriers are lactose, terra alba, sucrose, talcum, gelatin, agar, pectin, acacia, magnesium stearate and stearic acid. Examples of liquid carriers are syrup, peanut oil, olive oil and water.

If a solid carrier for oral administration is used, the preparation can be tableted, placed in hard gelatin capsule in powder or pellet form or in the form of a troche or lozenge. If a liquid carrier is used, the preparation may, for example, be in the form of syrup, an emulsion, a soft gelatin capsule, a sterile injectable solution or an aqueous or non-aqueous liquid suspension.

The compounds of this invention are active in a number of assays predictive for antipsychotic effect. In all models they show a strong anti-dopaminergic effect, both after intravenous and oral administration.

Table 1 shows the $ED_{50}$ values for selected compounds in the methylphenidate induced gnawing test in mice.

TABLE 1

| COMPOUND | $ED_{50}$ (mg/kg) |
|---|---|
| (+)-8-chloro-7-methoxymethyloxy-3-methyl-5-(benzofuran-7-yl)-2,3,4,5-tetrahydro-1H-3-benzazepine | 2.0 |
| (+)-8-chloro-7-methoxymethyloxy-3-methyl-5-(2,3-dihydrobenzofuran-7-yl)-2,3,4,5-tetrahydro-1H-3-benzazepine | 5.4 |

The 2,3,4,5-tetrahydro-1H-3-benzazepines of the general formula I can be prepared by the following method using starting materials prepared as described in U.S. Pat. No. 4,751,222:

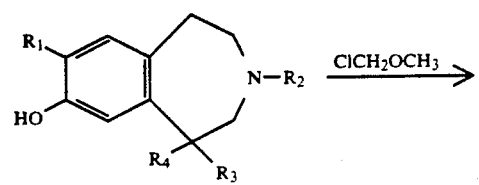

-continued

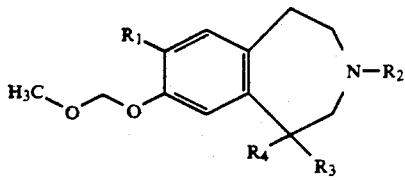

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05-100 mg in a pharmaceutically-acceptable carrier per unit dosage.

A typical tablet, which may be prepared by conventional tabletting techniques, contains:

| | |
|---|---|
| Active compound | 1.0 mg |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

The following examples illustrate the preparation of the novel compounds of this invention:

EXAMPLE 1

(+)-5-(7-benzofuranyl)-8-chloro-7-methoxymethyloxy-3-methyl-2,3,4,5-tetrahydro-1H-3-benzazepine (+)-5-(7-benzofuranyl)-8-chloro-3-methyl-2,3,4,5-tetrahydro-1H-3-benzazepin-7-ol (1.64 g, 0.005 mol) is suspended in dry ethanol (50 ml). Potassium-tert.-butylate (1.12 g, 0.010 mol) and potassiumiodide (0.10 g) are added. To the resulting solution chloromethyl methyl ether (0.84 g, 0.010 mol) is added. The reaction mixture is stirred for 3 hours. The resulting suspension is filtered and the filtrate evaporated to dryness under reduced pressure. The residue is chromatographed on a siliciagel column, using dichloromethane/methanol (25:1) as the eluent. The fractions containing the product are collected and evaporated to dryness under reduced pressure.

Yield: 1.17 g (63%) light yellow oil.

Microanalysis: Calc. for $C_{21}H_{22}ClNO_3$:C 67.8%, H 6.0%, N 3.8%. Found: C 67.5%, H 6.0%, N 3.6%.

Identity: NMR 400 mHz, $^1$H-chemical shifts in ppm. $CDCl_3$ as solvent, TMS as internal standard.

(δ, ppm): 2.39(S,3H); 2.43 (d,1H) 2.88 (M,2H); 3.16 (M,3H); 3.30 (S,3H); 4.76 (d,1H); 4.90 (Q,2H); 6.46 (S,1H); 6.82 (d,1H); 7.06 (d,1H); 7.20 (S,1H); 7.25 (t,1H), 7.57 (d,1H) and 7.62 (d,1H)

EXAMPLE 2

(+)-8-chloro-5-(2,3-dihydro-benzofuran-7-yl)-7-methoxy-methyloxy-3-methyl-2,3,4,5-tetrahydro-1H-3-benzazepine.

(+)-8-chloro-5-(2,3-dihydrobenzofuran-7-yl))-3-methyl-2,3,4,5-tetrahydro-1H-3-benzazepin-7-ol (4.95 g, 0.015 mol) and potassium-tert butylate (1.85 g, 0.016 mol) are dissolved in dry tetrahydrofuran (40 ml) at 5° C. Chloromethyl methyl ether (1.51 g, 0.019 mol) is added, the temperature raising to 35° C. The reaction mixture is stirred for three hours, then evaporated to dryness under reduced pressure. The residue is partitioned between water and toluene after adjusting the pH to 8.0 by addition of 1N sodiumhydroxide. The toluene phase is dried over magnesium sulphate, and evaporated to dryness under reduced pressure. The residue is crystallized from ethylacetate (11 ml).

Yield: 3.1 g (55%) white crystals. Mp: 111°-113° C.

Microanalysis: Calc. for $C_{21}H_{24}ClNO_3$: C 67.5%, H 6.5%, N 3.8%. Found: C 67.5%, H 6.6%, N 3.7%.

Identity: NMR 400 mHz., $^1$H-chemical shifts in ppm. $CDCl_3$ as solvent, TMS as internal standard.

(δ, ppm): 2.37 (broad S,4H); 2.8-3.1 (M,5H); 3.23 (t,2H); 3.40 (S,3H) 4.40 (t,1H); 4.52 (t,2H); 5.00 (S,2H); 6.57 (S,1H); 6.83 (M,2H) and 7.14 (M,2H)

EXAMPLE 3

(+)-5-(2,3-dihydrobenzofuran-7-yl)-7-methoxymethyloxy-3-methyl-8-nitro-2,3,4,5-tetrahydro-1H-3-benzazepine.

(+)-5-(2,3-dihydrobenzofuran-7-yl)-3-methyl-8-nitro-2,3,4,5-tetrahydro-1H-3-benzazepin-7-ol (68.0 mg, 2.0 mmol) and potassium-tert-butylate (24.0 mg, 2.2 mmol) are dissolved in dry tetrahydrofuran (10 ml) at 23° C. Chloromethyl methyl ether (20.0 mg, 2.5 mmol) is added. The reaction mixture is stirred for 22 hours, filtered and the filtrate evaporated to dryness under reduced pressure. The resulting light yellow oil is purified using reverse phase HPLC (column 16 mm×250 mm, $C_{18}$ 7μ; eluent aceticnitril/0.1M ammoniumsulphate pH 3.3 (30:70), isocratic). The fractions containing the product are pooled. The pH is adjusted to 9.0, and the product extracted into dichloromethane. The organic phase is evaporated to dryness under reduced pressure.

Yield: 30 mg (39%), light yellow oil.

EXAMPLE 4

(+)-5-(2,3-dihydrobenzofuran-7-yl)-8-iodo-7-methoxymethyloxy-3-methyl-2,3,4,5-tetrahydro-1H-3-benzazepine (+)-5-(2,3-dihydrobenzofuran-7-yl)-8-iodo-3-methyl-2,3,4,5-tetrahydro-1H-3-benzazepin-7-ol (126.0 mg, 3.0 mmol) and potassiumm-tert-butylate 37.0 mg, 3.3 mmol) are dissolved in dry tetrahydrofuran (10 ml) at 20° C. Chloromethyl methyl ether (30.0 mg, 3.8 mmol) is added. The reaction mixture is stirred for 3.5 hours then poured into 5% sodiumhydrogencarbonate (20 ml). The product is extracted into dichloromethane (2×15 ml). The organic phase is evaporated to dryness under reduced pressure.

Yield 100 mg (71%), yellow oil.

The product is purified by reverse phase HPLC as discribed in example 3.

EXAMPLE 5

8-chloro-7-methoxymethyloxy-3-methyl-5-(1,2,3,4-tetrahydronapth-6-yl)-2,3,4,5-tetrahydro-1-H-3-benzazepine 8-chloro-3-methyl-5-(1,2,3,4-tetrahydronapth-6-yl)-2,3,4,5-tetrahydro-1H-3-benzazepin-7-ol (103.0 mg, 3.0 mmol) and potassium-tert-butylate (37.0 mg, 3.3 mmol) are dissolved in dry tetrahydrofuran (10 ml) at 20° C. Chloromethyl methyl ether (30.0 mg, 3.8 mmol) is added. The reaction mixture is stirred for two days, then poured into 5% sodiumhydrogencarbonate (20 ml). The product is extracted into dicloromethane (2×15 ml), and the organic phase is evaporated to dryness under reduced pressure.

Yield: 95 mg (82%) light yellow oil.

The product is purified by reverse phase HPLC as discribed in example 3.

We claim:

1. A compound of formula I

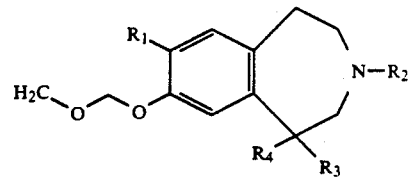

wherein
$R^1$ is hydrogen, halogen or nitro;
$R^2$ and $R^3$ are hydrogen or $C_{1-6}$-alkyl; and
$R^4$ is pyridyl or a ring system consisting of phenyl ortho condensed with benzene, cyclohexane, cyclohexene, cyclopentane or cyclopentene wherein one of the carbon atoms of the ortho fused ring, (a) which carbon atom is single bonded to two other carbon atoms, may be exchanged with oxygen, sulphur or NH or (b) which carbon atom is single bonded to one carbon atmo and double bonded to another carbon atom, may be exchanged with nitrogen; or a pharmaceutically acceptable salt thereof.

2. A pharmaceutical composition comprising (a) an effective amount of a compound of formula I

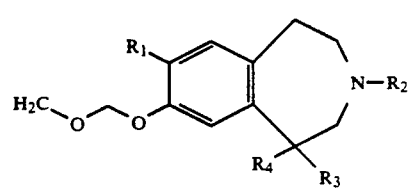

wherein
$R^1$ is hydrogen, halogen or nitro;
$R^2$ and $R^3$ are hydrogen or $C_{1-6}$-alkyl; and
$R^4$ is pyridyl or a ring system consisting of phenyl ortho condensed with benzene, cyclohexane, cyclohexene, cyclopentane or cyclopentene wherein one of the carbon atoms of the ortho fused ring, (a) which carbon atom is single bonded to two other carbon atoms, may be exchanged with oxygen, sulphur or NH or (b) which carbon atom is single bonded to one carbon atom and double bonded to another carbon atom, may be exchanged with nitrogen; or a pharmaceutically acceptable salt thereof; and (b) a pharmaceutically acceptable carrier or diluent.

3. A method of treating a central nervous system ailment sensitive to the dopamine D1-receptor, in a subject in need thereof, which comprises administering to said subject (a) an effective amount of a dopamine D1-antagonist of formula I

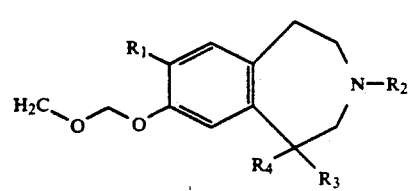

wherein
$R^1$ is hydrogen, halogen or nitro;
$R^2$ and $R^3$ are hydrogen or $C_{1-6}$-alkyl; and $R^4$ is pyridyl or a ring system consisting of phenyl ortho condensed with benzene, cyclohexane, cyclohexene, cyclopentane or cyclopentene wherein one of the carbon atoms of the ortho fused ring, (a) which carbon atom is single bonded to two other carbon atoms, may be exchanged with oxygen, sulphur or NH or (b) which carbon atom is single bonded to one carbon atom and double bonded to another carbon atom, may be exchanged with nitrogen; or a pharmaceutically acceptable salt thereof; and (b) a pharmaceutically acceptable carrier or diluent.

4. A compound according to claim 1 which is (+)-5-(7-benzofuranyl)-8-chloro-7-methoxymethyloxy-3-methyl-2,3,4,5-tetrahydro-1H-3-benzazepine or a pharmaceutically acceptable salt thereof.

5. A compound according to claim 1 which is (+)-8-chloro-5-(2,3-dihydro-benzofuran-7-yl)-7-methoxymethyloxy-3-methyl-2,3,4,5-tetrahydro-1H-3-benzazepine or a pharmaceutically acceptable salt thereof.

6. A compound according to claim 1 which is (+)-5-(2,3-dihydrobenzofuran-7yl)-7-methoxymethyloxy-3-methyl-8-nitro-2,3,4,5-tetrahydro-1H-3-benzazepine or a pharmaceutically acceptable salt thereof.

7. A compound according to claim 1 which is (+)-5-(2,3-dihydrobenzofuran-7-yl)-8-iodo-7-methoxymethyloxy-3-methyl-2,3,4,5-tetrahydro-1H-3-benzazepine or a pharmaceutically acceptable salt thereof.

8. A compound according to claim 1 which is 8-chloro-7-methoxymethyloxy-3-methyl-5-(1,2,3,4-tetrahydronaphth-6-yl)-2,3,4,5-tetrahydro-1H-3-benzazepine or a pharmaceutically acceptable salt thereof.

9. The pharmaceutical composition according to claim 2 in the form of an oral dosage unit containing about 0.5 mg to 1000 mg of the active compound.

10. The method according to claim 3 wherein said compound is administered in the form of an oral dosage unit containing about 0.5 mg to 1000 mg of the active compound.

11. The method according to claim 3 wherein said compound is administered in the form of a pharmaceutical composition together with a pharmaceutically acceptable carrier or diluent.

12. The method according to claim 3 wherein the compound of Formula I is selected from the group consisting of
(+)-5-(7-benzofuranyl)-8-chloro-7-methoxymethyloxy-3-methyl-2,3,4,5-tetrahydro-1H-3-benzazepine;
(+)-8-chloro-5-(2,3-dihydro-benzofuran-7-yl)-7-methoxymethyloxy-3-methyl-2,3,4,5-tetrahydro-1H-3-benzazepine;
(+)-5-(2,3-dihydrobenzofuran-7-yl)-7-methoxymethyloxy-3-methyl-8-nitro-2,3,4,5-tetrahydro-1H-3-benzazepine;
(+)-5-(2,3-dihydrobenzofuran-7-yl)-8-iodo-7-methoxymethyloxy-3-methyl-2,3,4,5-tetrahydro-1H-3-benzazepine; and
8-chloro-7-methoxymethyloxy-3-methyl-5-(1,2,3,4-tetrahydronaphth-6-yl)-2,3,4,5-tetrahydro-1H-3-benzazepine, or a pharmaceutically acceptable salt thereof.

* * * * *